US009763887B2

(12) United States Patent
Loughlin et al.

(10) Patent No.: US 9,763,887 B2
(45) Date of Patent: Sep. 19, 2017

(54) MESALAMINE PHARMACEUTICAL COMPOSITION WITH MULTIPLE DOSAGE ELEMENTS FOR REDUCED DELIVERY VARIABILITY

(71) Applicant: Warner Chilcott Company, LLC, Fajardo, PR (US)

(72) Inventors: Ryan Gerald Loughlin, Crumlin (IE); Stephen McCullagh, Belfast (IE); Roger Boissonneault, Morristown, NJ (US)

(73) Assignee: Allergan Pharmaceuticals International Limited, Dublin (IE)

( * ) Notice: Subject to any disclaimer, the term of this patent is extended or adjusted under 35 U.S.C. 154(b) by 0 days.

(21) Appl. No.: 14/210,850

(22) Filed: Mar. 14, 2014

(65) Prior Publication Data
US 2014/0271859 A1 Sep. 18, 2014

Related U.S. Application Data

(60) Provisional application No. 61/794,998, filed on Mar. 15, 2013.

(51) Int. Cl.
*A61K 9/28* (2006.01)
*A61K 31/196* (2006.01)
*A61K 9/48* (2006.01)
*A61K 31/606* (2006.01)

(52) U.S. Cl.
CPC .......... *A61K 9/2846* (2013.01); *A61K 9/2886* (2013.01); *A61K 9/4808* (2013.01); *A61K 31/606* (2013.01)

(58) Field of Classification Search
None
See application file for complete search history.

(56) References Cited

U.S. PATENT DOCUMENTS

| | | | |
|---|---|---|---|
| 4,432,966 A | 2/1984 | Zeitoun et al. | |
| 4,910,021 A | 3/1990 | Davis et al. | |
| 5,171,580 A | 12/1992 | Iamartino et al. | |
| 5,316,772 A | 5/1994 | Jurgens, Jr. et al. | |
| 5,401,512 A | 3/1995 | Rhodes et al. | |
| 5,482,718 A | 1/1996 | Shah et al. | |
| 5,541,170 A | 7/1996 | Rhodes et al. | |
| 5,541,171 A | 7/1996 | Rhodes et al. | |
| 5,654,004 A | 8/1997 | Okayama et al. | |
| 5,686,105 A | 11/1997 | Kelm et al. | |
| 5,686,106 A | 11/1997 | Kelm et al. | |
| 5,900,252 A | 5/1999 | Calanchi et al. | |
| 5,914,132 A | 6/1999 | Kelm et al. | |
| 6,551,620 B2 | 4/2003 | Otterbeck | |
| 6,773,720 B1 | 8/2004 | Villa et al. | |
| 6,893,662 B2 | 5/2005 | Dittmar et al. | |
| 8,337,886 B2 | 12/2012 | Otterbeck | |
| 8,496,965 B2 | 7/2013 | Otterbeck | |
| 8,865,688 B2 | 10/2014 | Forbes | |
| 8,911,778 B2 | 12/2014 | Otterbeck et al. | |
| 8,940,328 B2 | 1/2015 | Otterbeck et al. | |
| 8,956,647 B2 | 2/2015 | Otterbeck et al. | |
| 2002/0034541 A1* | 3/2002 | Valducci | 424/464 |
| 2012/0093939 A1* | 4/2012 | Payne et al. | 424/497 |

FOREIGN PATENT DOCUMENTS

| | | |
|---|---|---|
| EP | 0225189 A1 | 11/1986 |
| EP | 1172100 A1 | 1/2002 |
| EP | 1315481 A1 | 12/2006 |
| WO | 0217887 A1 | 3/2002 |

OTHER PUBLICATIONS

Ibekwe et al, "Interplay between intestinal pH, transit time and feed status on the in vivo performance of pH responsive ileo-colonic release systems", Pharmaceutical Research, vol. 25, No. 8, pp. 1828-1835 (Aug. 2008).
Ibekewe et al, "A comparative in vitro assessment of the drug release performance of pH-responsive polymers for ileo-colonic delivery", Journal of Pharmaceutical Sciences, vol. 308, pp. 52-60 (2006).
Safdi "Determination of 5-ASA in Whole or Partial Mesalamine Delayed-Release Tablets Recovered from Fecal Samples of Healthy Volunteers", American Journal of Gasteroenterology, S159 (2005).
Sinha, et al., "Intestinal Performance of Two Mesalamine Formulation in Patients with Active Ulcerative Colitis as Assessed by Gamma Scintigraphy", Practical Gastroenterology, pp. 56-69 (Oct. 2003).
McConnell, et. al., "Gut instincts: Explorations in intestinal physiology and drug delivery", International Journal of Pharmaceutics, vol. 364, pp. 213-226 (2008).
Khan, et al., "A pH-Dependent Colon-Targeted Oral Drug Delivery System Using Methacrylic Acid Copolymers. II. Manipulation of Drug Release Using Eudragit® L100 and Eudragit S100 Combinations", Drug Development and Industrial Pharmacy, vol. 26, No. 5, pp. 549-554 (2000).

(Continued)

*Primary Examiner* — Robert A Wax
*Assistant Examiner* — Danah Al-Awadi
(74) *Attorney, Agent, or Firm* — Fitzpatrick, Cella, Harper & Scinto

(57) ABSTRACT

A mesalamine pharmaceutical composition with reduced delivery variability for delivery of mesalamine to the colon that includes multiple dosage elements, and each dosage element includes mesalamine and an enteric coating. The enteric coating of each different dosage element differs so the release point of the mesalamine in the GI tract is varied. In one embodiment, a first dosage element releases about 30% to about 60% by weight of the total mesalamine in the composition after 60 minutes at a pH of about 6.6 in an aqueous phosphate buffer using a paddle apparatus 2 with a paddle speed of 100 rpm and a second dosage element releases about 40% to about 70% by weight of the total mesalamine after 60 minutes at a pH of about 7.2 in an aqueous phosphate buffer using a paddle apparatus 2 with a paddle speed of 100 rpm.

11 Claims, 4 Drawing Sheets

(56) References Cited

OTHER PUBLICATIONS

International Search Report and Written Opinion from PCT Application No. PCT/US20014/027353 mailed Jun. 23, 2014.
Fallingborg, Dan Med. Bull., 46:183-96 (1999).
First Office Action in Chinese Application No. 201480022816.2 (Apr. 19, 2017).

* cited by examiner

MESALAMINE PHARMACEUTICAL COMPOSITION WITH MULTIPLE DOSAGE ELEMENTS FOR REDUCED DELIVERY VARIABILITY

CROSS-REFERENCE TO RELATED APPLICATION

This application claims the benefit of U.S. Provisional Patent Application No. 61/794,998, filed Mar. 15, 2013, the entire disclosure of which is incorporated by reference herein.

BACKGROUND OF THE INVENTION

Field of the Invention

This invention relates to a mesalamine pharmaceutical composition. In particular, it relates to a mesalamine pharmaceutical composition that has a reduced delivery variability.

Description of Related Art

The advantages of delivery of therapeutic agents to the lower part of the gastrointestinal tract, especially the large intestine or the colon, are well known. Several references illustrate the difficulty of formulating dosage forms that will achieve this delivery benefit. For example, U.S. Pat. Nos. 5,541,170 and 5,541,171 (both Rhodes et al.) discuss the delivery of pharmacologically active agents, especially 5-aminosalicylic acid, to the large intestine for the treatment of colonic or rectal disorders. U.S. Pat. No. 5,686,105 (Kelm et al.) teaches colonic delivery of therapeutic agents wherein the dosage form comprises a coating system with at least one inner coating layer and one outer coating layer. The inner coating layer is an enteric polymer that begins to dissolve in an aqueous media at a pH between about 5 to about 6.3, and the outer coating layer is an enteric polymer that begins to dissolve in an aqueous media at a pH of between about 6.8 to 7.2. U.S. Pat. No. 5,171,580 (Iamartino et al.) teaches pharmaceutical preparations containing an active ingredient to be released in the lower part of the gastrointestinal tract, the large intestine and especially the colon, consisting of a core with the active, the core being coated with three protective layers at different solubilities. This reference focuses on providing more specific and reliable release of a therapeutic active agent to the lower part of the gastrointestinal tract, especially the colon, achieved with the three protection layers, as well as the benefits of having a selective effect in the colon.

Other references also focus on the benefits of delivering therapeutic agents to the colon. These references include U.S. Pat. No. 5,686,106 (Kelm et al.), U.S. Pat. No. 5,914,132 (Kelm et al.), U.S. Pat. No. 4,910,021 (Davis et al.), U.S. Pat. No. 4,432,966 (Zeitoun et al.), U.S. Pat. No. 5,654,004 (Okayama et al.), U.S. Pat. No. 5,900,252 (Calcanchi et al.), U.S. Pat. No. 5,482,718 (Shah et al.), U.S. Pat. No. 5,316,772 (Jurgens et al.), U.S. Pat. No. 5,401,512 (Rhodes et al.), EP 225,189 (Davies, et al.), EP 1315481 (Lutolf et al.), and Khan et al., Drug Development and Industrial Pharmacy, 26(5), 549-554 (2000).

U.S. Pat. No. 6,893,662 (Dittmar et al.) teaches a solid unit dosage form for oral administration which minimizes the impact or negative effects of coating fractures, especially for larger or heavier unit dosage forms.

The problem of mesalamine tablets and other similar tablets passing through the gut intact have been described in Sinha et al., Pract. Gastroenterol., 27, 56-69 (2003), Safdi, Am. J. Gasteroenterol., 5159 (2005), Ibekwa et al., J. Pharm. Sci., 308, 52-60 (2006), and Ibekwa et al., Pharm. Res., 25, 1828-1835 (2008). McConnell et al., Intl. J. Pharms., 364, 213-226 (2008) have found that due to variations in the physiology of the gastrointestinal tract from person to person, the failure to disintegrate may be due to the target pH not being reached in some subjects or not being high enough for a long time for the pH-responsive film coating to dissolve. Such failure to disintegrate results in delivery variability of the mesalamine pharmaceutical compositions.

Accordingly, there remains a need for mesalamine pharmaceutical composition which reduces delivery variability by minimizing the failure to disintegrate.

SUMMARY OF THE INVENTION

The present invention is directed to a mesalamine pharmaceutical composition for delivery of mesalamine to the colon with reduced delivery variability. The composition comprises (i) at least one first dosage element comprising a first mesalamine dose and a first enteric coating and (ii) at least one second dosage element comprising a second mesalamine dose and a second enteric coating, wherein the first enteric coating is soluble at a pH of 6.4 to 6.8 in an aqueous phosphate buffer and the second enteric coating is soluble in an aqueous phosphate buffer at a pH of 0.2 to 1 units higher than the first enteric coating. As used herein, an enteric coating is soluble at a pH in an aqueous phosphate buffer when after 60 minutes at least 70%, preferably at least 85% of the mesalamine within the enteric coating has been released (dissolved) using a paddle apparatus 2 with a paddle speed of 100 rpm. The solubility of the enteric coating is being measured based on release of mesalamine from the dosage element. Specifically, in this first embodiment, all determinations of solubility of the enteric coatings "at a pH in aqueous phosphate buffer" are made after an initial treatment regimen first exposing the composition to 0.1 N hydrochloric acid for 2 hours at a paddle speed of 100 rpm followed by exposure to pH 6.0 phosphate buffer for 1 hour at a paddle speed of 100 rpm.

In a first embodiment, the solubility of the enteric coating of the dosage element is measured in accordance with the present invention by subjecting the dosage element to an initial treatment regimen first exposing the composition to 0.1 N hydrochloric acid for 2 hours at a paddle speed of 100 rpm followed by exposure to pH 6.0 phosphate buffer for 1 hour at a paddle speed of 100 rpm and determining the pH at which at least 70%, preferably at least 85%, of the mesalamine within the enteric-coated dosage element has been released. Thus, for purposes of the solubility measured, in one embodiment of the invention each dosage element in the composition, e.g., first dosage element and second dosage element, is tested separately, i.e., using a different phosphate buffer having a different pH after the exposure to 0.1 N hydrochloric acid and pH 6.0 phosphate buffer. In this embodiment the test includes three stages, i.e., 0.1N HCL, pH 6.0 phosphate buffer and a selected pH phosphate buffer (e.g., pH 6.4, 6.6, 6.8, 7.0, 7.2 or 7.4). In yet another embodiment of the invention, solubility may be determined by conducting the test on all the dosage elements at once over a set of four sequential stages, i.e., sequential exposure to 0.1 N HCL (2 hours), 6.0 pH phosphate buffer (1 hour), a first selected pH phosphate buffer (1 hour), and a second selected pH phosphate buffer (1 hour). The second selected phosphate buffer is always a higher pH than the first selected pH buffer, e.g., pH 7.2 and pH 6.6, respectively. In a preferred embodiment, the first enteric coating is determined to be soluble based on mesalamine release (at least 75%) at a pH of about 6.6 in an aqueous phosphate buffer and the second enteric coating is determined to be soluble based on mesalamine release (at least 75%) at a pH of about 7.2 in an aqueous buffer.

In a first embodiment, the at least one first dosage element releases mesalamine in an amount of about 30% to about 60% by weight of the mesalamine in the composition over 60 minutes at a pH of about 6.6 in an aqueous phosphate buffer using a paddle apparatus 2 with a paddle speed of 100 rpm, and the at least one second dosage element releases mesalamine in an amount of at least about 40% to about 70% by weight of the mesalamine in the composition over 60 minutes at a pH of about 7.2 in an aqueous phosphate buffer using a paddle apparatus 2 with a paddle speed of 100 rpm. The enteric coatings, e.g. the first and second enteric coatings, of the at least first and second dosage elements are different. By different it is meant that the enteric coatings may be of the same material, but differ in thickness that provides for a different release time at a given pH or the enteric coatings may be of a different enteric composition having a different solubility, e.g., time to 70% release, at a given pH in an aqueous phosphate buffer using a paddle apparatus 2 with a paddle speed of 100 rpm.

A second embodiment of the present invention is directed to a mesalamine pharmaceutical composition for delivery of mesalamine to the colon with reduced delivery variability. The composition comprises (i) at least one first dosage element comprising a first mesalamine dose and a first enteric coating and (ii) at least one second dosage element comprising a second mesalamine dose and a second enteric coating, wherein the first enteric coating is soluble at a pH of 5.9 to less than 6.4 in an aqueous phosphate buffer and the second enteric coating is soluble in an aqueous phosphate buffer at a pH of 0.2 to 1.3 units higher than the first enteric coating. As used herein, an enteric coating is soluble at a pH in an aqueous phosphate buffer when after 60 minutes at least 70%, preferably at least 85% of the mesalamine within the enteric coating has been released (dissolved) using a paddle apparatus 2 with a paddle speed of 100 rpm. The solubility of the enteric coating is being measured based on release of mesalamine from the dosage element. Specifically, in this second embodiment, all determinations of solubility of the enteric coatings "at a pH in aqueous phosphate buffer" are made after an initial treatment regimen first exposing the composition to 0.1 N hydrochloric acid for 2 hours at a paddle speed of 100 rpm followed by exposure to pH 5.5 phosphate buffer for 1 hour at a paddle speed of 100 rpm.

In a second embodiment, the solubility of the enteric coating of the dosage element is measured in accordance with the present invention by subjecting the dosage element to an initial treatment regimen first exposing the composition to 0.1 N hydrochloric acid for 2 hours at a paddle speed of 100 rpm followed by exposure to pH 5.5 phosphate buffer for 1 hour at a paddle speed of 100 rpm and determining the pH at which at least 70%, preferably at least 85%, of the mesalamine within the enteric-coated dosage element has been released. In this second embodiment, all determinations of solubility of the enteric coatings "at a pH in aqueous phosphate buffer" are made after an initial treatment regimen first exposing the composition to 0.1 N hydrochloric acid for 2 hours at a paddle speed of 100 rpm followed by exposure to pH 5.5 phosphate buffer for 1 hour at a paddle speed of 100 rpm. Thus, for purposes of the solubility measured, in one embodiment of the invention each dosage element in the composition, e.g., first dosage element and second dosage element, is tested separately, i.e., using a different phosphate buffer having a different pH after the exposure to 0.1 N hydrochloric acid and pH 5.5 phosphate buffer. In this second embodiment the test includes three stages, i.e., 0.1N HCL, pH 5.5 phosphate buffer and a selected pH phosphate buffer (e.g., pH 6.0, 6.1, 6.2 or 6.3). In yet another embodiment of the invention, solubility may be determined by conducting the test on all the dosage elements at once over a set of four sequential stages, i.e., sequential exposure to 0.1 N HCL (2 hours), 5.5 pH phosphate buffer (1 hour), a first selected pH phosphate buffer (1 hour), and a second selected pH phosphate buffer (1 hour). The second selected phosphate buffer is always a higher pH than the first selected pH buffer, e.g., pH 7.0 and pH 6.0, respectively. In a preferred embodiment, the first enteric coating is determined to be soluble based on mesalamine release (at least 75%) at a pH of about 6.0 in an aqueous phosphate buffer and the second enteric coating is determined to be soluble based on mesalamine release (at least 75%) at a pH of about 6.6 in an aqueous buffer. In a second preferred embodiment, the first enteric coating is determined to be soluble based on mesalamine release (at least 75%) at a pH of about 6.0 in an aqueous phosphate buffer and the second enteric coating is determined to be soluble based on mesalamine release (at least 75%) at a pH of about 7.0 in an aqueous buffer.

In a second embodiment, the at least one first dosage element releases mesalamine in an amount of about 30% to about 60% by weight of the mesalamine in the composition over 60 minutes at a pH of about 6.0 in an aqueous phosphate buffer using a paddle apparatus 2 with a paddle speed of 100 rpm, and the at least one second dosage element releases mesalamine in an amount of at least about 40% to about 70% by weight of the mesalamine in the composition over 60 minutes at a pH of about 6.6 in an aqueous phosphate buffer using a paddle apparatus 2 with a paddle speed of 100 rpm. In this second embodiment, all determinations of solubility of the enteric coatings "at a pH in aqueous phosphate buffer" are made after an initial treatment regimen first exposing the composition to 0.1 N hydrochloric acid for 2 hours at a paddle speed of 100 rpm followed by exposure to pH 5.5 phosphate buffer for 1 hour at a paddle speed of 100 rpm. The enteric coatings, e.g. the first and second enteric coatings, of the at least first and second dosage elements are different. By different it is meant that the enteric coatings may be of the same material, but differ in thickness that provides for a different release time at a given pH or the enteric coatings may be of a different enteric composition having a different solubility, e.g., time to 70% release, at a given pH in an aqueous phosphate buffer using a paddle apparatus 2 with a paddle speed of 100 rpm.

In one embodiment of the present invention, the pH at which the second coating is soluble is 0.4 to 0.8 higher than the pH at which the first enteric coat is soluble. In another embodiment of the present invention, the pH at which the second enteric coating is soluble is 0.5 to 0.6 higher than the pH at which the first enteric coat is soluble. In yet another embodiment of the present invention, the pH at which the second enteric coating is soluble is 0.9 to 1.1, preferably 1.0, higher than the pH at which the first enteric coat is soluble.

DETAILED DESCRIPTION OF THE INVENTION

Figure 1:
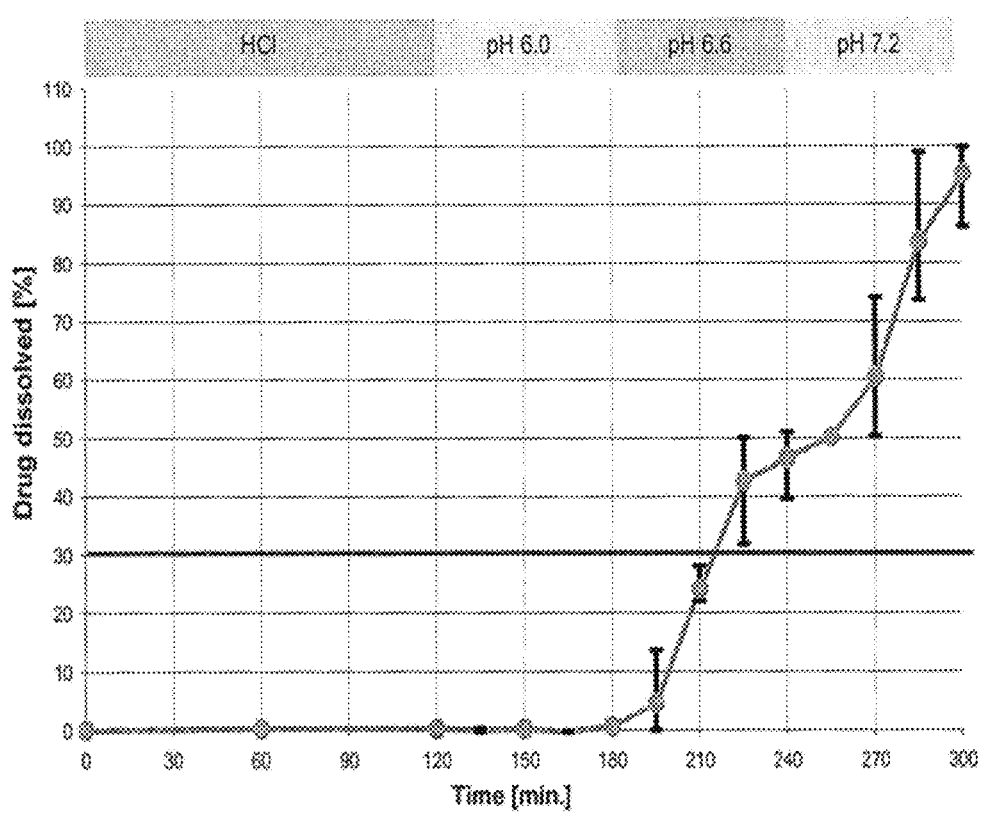
FIG. 1 is a plot depicting the dissolution profile of a mesalamine pharmaceutical composition of an embodiment of the present invention.

An embodiment of the present invention is directed to a mesalamine pharmaceutical composition for delivery of mesalamine to the colon with reduced delivery variability. The composition comprises at least one first dosage unit and at least one second dosage unit. If desired the composition may comprise a plurality of different dosage elements, e.g., three, four, etc., each being comprised of mesalamine and a different enteric coating, i.e., enteric coatings having a different solubility defined by the pH in an aqueous buffer solution at which in 60 minutes at least 70%, preferably at least 85% of mesalamine is released by the enteric coating using a paddle apparatus 2 with a paddle speed of 100 rpm.

The at least one first dosage element generally will contain 30 to 70% by weight of the total mesalamine in the composition and the at least one second dosage element generally contain 30% to 70% by weight of the total mesalamine in the composition. In another embodiment, the at least one first dosage element contains about 50% by weight of the total mesalamine in the composition and the at least one second dosage element contains about 50% by weight of the total mesalamine in the composition.

Delivery of mesalamine to the colon is of critical importance when treating diseases associated with the colon such as ulcerative colitis and IBD. If the enteric coating of the pharmaceutical composition fails to dissolve such that the dosage form fails to open and release mesalamine due to an individual's pH variation within gastrointestinal tract, then that individual will not receive delivery of mesalamine necessary to effectively treat the disorder. The inventors of the present invention found that it is possible to minimize the problem of delivery failure of enterically coated mesalamine pharmaceutical compositions by providing a composition having at least two dosage elements having different dissolution profiles.

One way to achieve different dissolution profiles for the at least two dosage elements is to vary the enteric coating for each of the dosage elements. This may be done by changing the thickness or other properties or characteristics of the enteric coating or more preferably by providing enteric coatings that are different in compositional makeup.

In one embodiment of the present invention, the mesalamine pharmaceutical composition comprises two dosage elements, i.e., a first and second dosage element having, respectively, a first and second enteric coating. It should be apparent that there may be a plurality of first dosage elements and second dosage elements in the pharmaceutical composition of the invention, e.g., a capsule may contain two first dosage elements and two second dosage units or three first dosage units and three second dosage units. There is no requirement that the same number of first and second dosage units be present so long as there is at least one of each. As previously noted, the pharmaceutical composition of the invention may include more than two different dosage elements as desired. The dosage elements used in the invention generally are comprised of mesalamine and any desired pharmaceutically acceptable excipients surrounded by the enteric coating. Preferably these dosage elements are placed in a capsule for delivery of the pharmaceutical composition of the invention, although it is also possible to deliver a tablet that is comprised of at least two dosage elements sandwiched together, preferably with an adhesive that is soluble in the stomach.

In an embodiment of the present invention, the first enteric coating of the first dosage element and the second enteric coating of the second dosage element may each independently be a single enteric coating of a single enteric polymer, for example, poly(methacrylic acid, methyl methacrylate) 1:2 (Eudragit® S) or poly(methacrylic acid, methyl methacrylate) 1:1 (Eudragit® L), or independently may be comprised of a combination of enteric polymers or even a combination of layers of different enteric polymers. In some embodiments of the present invention, the first enteric coating of the first dosage element may be a mixture of poly(methacrylic acid, methyl methacrylate) 1:2 (Eudragit® S) and poly(methacrylic acid, methyl methacrylate) 1:1 (Eudragit® L) and the second enteric coating of the second dosage element may be selected from the group consisting of poly(methacrylic acid, methyl methacrylate) 1:2 and poly(methacrylic acid, methyl methacrylate) 1:1. In a preferred embodiment of the present invention, the second enteric coating of the second dosage element is Eudragit® S. In yet another embodiment of the present invention, the first enteric coating of the first dosage element is a mixture of Eudragit® S 12.5 and Eudragit® L 12.5 and the second enteric coating of the second dosage element is Eudragit® S 12.5. In another preferred embodiment of the present invention, the first enteric coating of the first dosage element is a comprises Eudragit® L 100 or Eudragit® L 12.5. In another embodiment, the first enteric coating of the first dosage element comprises mixtures of poly(methacrylic acid-co-ethyl acrylate) 1:1 (e.g., Eudragit® L 30 D-55 or 100 55) with one of the foregoing methacrylate co-polymers, such as Poly(methacrylic acid-co-methyl methacrylate) 1:2 (e.g., Eudragit® S 100) or poly(methacylic acid-co-methyl methacrylate) 1:1 (1:1) (e.g., Eudragit® L 30 D-55 or 100 55). A person of ordinary skill will recognize that enteric polymers may be used singly to form an eneteric coating or combined. Such exemplary enteric polymers are available from Evonik Industries and include for example Eudragit® L 30 D-55 and Eudragit® L-100-55 (each with a reported dissolution property of above pH 5.5), Eudragit® L 100 and Eudragit L12.5 (each with a reported dissolution property above pH 6.0), and Eudragit® S100, Eudragit® S12.5 and Eudragit® FS 30D (each with a reported dissolution property above pH 7.0). Combinations of one or more of the foregoing polymers, or other enteric polymers known in the art, may be made to create enteric coatings that dissolve at the desired pH required by the invention.

In an embodiment of the present invention, the mesalamine pharmaceutical composition comprises two dosage elements and the mixing weight ratio of the first enteric coating of the first dosage is 9:1 to 1:9. In a preferred embodiment of the present invention, the mixing weight ratio of the first enteric coating of the first dosage element is 6:4 to 4:6, more preferably 5:5.

In an embodiment of the present invention, the mesalamine pharmaceutical composition comprises a capsule with multiple tablets with different types of enteric coatings. In a preferred embodiment of the present invention, the mesalamine pharmaceutical composition comprises a capsule with multiple tablets with at least two different types of enteric coatings.

In another embodiment of the present invention, the mesalamine pharmaceutical composition comprises a capsule with multiple mini tablets with different types of enteric coatings. In a preferred embodiment of the present invention, the composition comprises a capsule with multiple mini tablets with at least two different types of enteric coatings. In another embodiment of the present invention, the mini tablets have a diameter of about 2.0 mm to about 10.0 mm, more preferably, about 4.0 mm to about 6.0 mm. In another embodiment of the present invention, the mini tablets have a diameter of about 6.0 mm. The capsules used to hold the dosing elements of the invention need only be sized with adequate volume to hold the dosage elements. Commercially available size 0el (Europe), size 0 or size AAel capsules may be used if desired.

In a first embodiment of the present invention, the first dosage element releases about 30 to about 60%, preferably about 35% to about 55%, more preferably about 40% to about 50% by weight of the total amount of mesalamine in the composition over 60 minutes at a pH of about 6.6 in an aqueous phosphate buffer using a paddle apparatus 2 with a paddle speed of 100 rpm. The second dosage element releases the remaining mesalamine in the composition while at a pH of about 7.2 in an aqueous phosphate buffer using a paddle apparatus 2 with a paddle speed of 100 rpm, i.e., at least 95% of the total mesalamine in the composition is released after the composition has been exposed in vitro to the about pH 6.6 aqueous phosphate buffer for 60 minutes followed by the about pH 7.2 aqueous phosphate buffer for 60 minutes under the conditions described above.

In a first embodiment of the present invention, the pH at which the second enteric coating is soluble is 0.4 to 0.8 higher than the pH at which the first enteric coat is soluble. In yet another embodiment of the present invention, the pH at which the second enteric coating is soluble is 0.5 to 0.6 higher than the pH at which the first enteric coating is soluble. In a preferred embodiment of the present invention, the composition comprises two dosage elements with different enteric coatings, and the first dosage element releases from about 85% to about 100% of the first mesalamine dose from the composition at a pH of about 6.6 in an aqueous phosphate buffer and the second dosage element releases from about 85% to 100% of the second mesalamine dose from the composition at a pH of about 7.2 in an aqueous phosphate buffer using a paddle apparatus 2 with a paddle speed of 100 rpm.

In a second embodiment of the present invention, the first dosage element releases about 30 to about 60%, preferably about 35% to about 55%, more preferably about 40% to about 50% by weight of the total amount of mesalamine in the composition over 60 minutes at a pH of about 6.0 in an aqueous phosphate buffer using a paddle apparatus 2 with a paddle speed of 100 rpm. The second dosage element releases the remaining mesalamine in the composition while at a pH of about 6.6 in an aqueous phosphate buffer using a paddle apparatus 2 with a paddle speed of 100 rpm, i.e., at least 95% of the total mesalamine in the composition is released after the composition has been exposed in vitro to the about pH 6.0 aqueous phosphate buffer for 60 minutes followed by the about pH 6.6 aqueous phosphate buffer for 60 minutes under the conditions described above.

In a second embodiment of the present invention, the pH at which the second enteric coating is soluble is 0.4 to 0.8 higher than the pH at which the first enteric coat is soluble.

In yet another embodiment of the present invention, the pH at which the second enteric coating is soluble is 0.5 to 0.6 higher than the pH at which the first enteric coating is soluble. In a preferred embodiment of the present invention, the composition comprises two dosage elements with different enteric coatings, and the first dosage element releases from about 85% to about 100% of the first mesalamine dose from the composition at a pH of about 6.0 in an aqueous phosphate buffer and the second dosage element releases from about 85% to 100% of the second mesalamine dose from the composition at a pH of about 6.6 in an aqueous phosphate buffer using a paddle apparatus 2 with a paddle speed of 100 rpm.

In another embodiment of the present invention, the first dosage element releases about 30 to about 60%, preferably about 35% to about 55%, more preferably about 40% to about 50% by weight of the total amount of mesalamine in the composition over 60 minutes at a pH of about 6.0 in an aqueous phosphate buffer using a paddle apparatus 2 with a paddle speed of 100 rpm. The second dosage element releases the remaining mesalamine in the composition while at a pH of about 7.0 in an aqueous phosphate buffer using a paddle apparatus 2 with a paddle speed of 100 rpm, i.e., at least 95% of the total mesalamine in the composition is released after the composition has been exposed in vitro to the about pH 6.0 aqueous phosphate buffer for 60 minutes followed by the about pH 7.0 aqueous phosphate buffer for 60 minutes under the conditions described above.

In a second embodiment of the present invention, the pH at which the second enteric coating is soluble is 0.9 to 1.1 higher than the pH at which the first enteric coat is soluble. In yet another embodiment of the present invention, the pH at which the second enteric coating is soluble is 1.0 higher than the pH at which the first enteric coating is soluble. In a preferred embodiment of the present invention, the composition comprises two dosage elements with different enteric coatings, and the first dosage element releases from about 85% to about 100% of the first mesalamine dose from the composition at a pH of about 6.0 in an aqueous phosphate buffer and the second dosage element releases from about 85% to 100% of the second mesalamine dose from the composition at a pH of about 7.0 in an aqueous phosphate buffer using a paddle apparatus 2 with a paddle speed of 100 rpm.

The drug release rate or dissolution rate of the various mesalamine pharmaceutical compositions may be determined according to USP dissolution apparatus II by direct spectrophotometry. Monitoring (quantitation of the amount of drug released) may be achieved using a US/VIS-detector, which detects the difference between the drug substance absorbance maximum and a non-absorbing wavelength. For consistency, the paddle apparatus 2 should be used with a paddle speed of 100 rpm.

The samples set forth and tested in the Examples below consisted of 1 capsule per vessel. Each capsule contained 4 tablets of mesalamine 100 mg. The dissolution media used in the tests set forth below (USP) was 0.1N HCl for 2 hours, followed by an increase in pH to 6.0 for 1 hour, followed by an increase in pH to 6.6 for 1 hour, followed by an increase in pH to 7.2 for 1 hour, as shown in Table 1 below.

TABLE 1

| | Acid Stage | Stage 1 | Stage 2 | Stage 3 |
|---|---|---|---|---|
| Media Volume | 0.1 N HCl 500 ml | pH 6.0 900 ml | pH 6.6 900 ml | pH 7.2 900 ml |

TABLE 1-continued

|  | Acid Stage | Stage 1 | Stage 2 | Stage 3 |
| --- | --- | --- | --- | --- |
| Paddle speed | 100 rpm | 100 rpm | 100 rpm | 100 rpm |
| Wave length | 302 nm | 330 nm | 330 nm | 330 nm |

The temperature of the solutions was maintained at 37° C.±0.5° C. The dissolution was measured at 1 h, 2 h, 2.25 h, 2.50 h, 2.75 h, 3 h, 3.25 h, 3.50 h, 3.75 h, 4 h, 4.25 h, 4.50 h, 5 h. The dissolution was measured using the method of USP monograph for "Mesalamine Delayed-Release Tablets" (USP29-NF24 Page 1355) for the Acid Stage and for Stage 1, followed by the tests described herein for Stage 2 and Stage 3.

Specific embodiments of the invention will now be demonstrated by reference to the following examples. It should be understood that these examples are disclosed by way of illustrating the invention and should not be taken in any way to limit the scope of the present invention.

EXAMPLES

In order to study the release or dissolution profiles of mesalamine pharmaceutical formulations of the present invention, mesalamine 100 mg mini-tablets were prepared as described below. First, the mesalamine tablet core was protected by a thin organic based pre-isolation layer comprising Eudragit® L 12.5 or Eudragit® S 12.5 and a plasticizer. Next, a functional coating layer was applied. This layer was also an organic based layer and comprised talc as a glidant, iron oxide red and iron oxide yellow as pigments and dibutyl sebacate as a plasticizer, and water to enhance film formation quality. The trigger pH was adjusted by using different mixtures of Eudragit® L 12.5 and Eudragit® S 12.5. The formulations of the mesalamine 100 mg mini-tablets are set forth in Tables 2-5.

TABLE 2

| Example 1 | Pre-isolation Layer | Functional Layer | Units |
| --- | --- | --- | --- |
| EUDRAGIT ® S 12.5 |  | 6.00 | mg/cm² |
| EUDRAGIT ® L 12.5 | 0.19 | — | mg/cm² |
| Talc Pharma |  | 27.45 | % on polymer |
| Iron oxide red |  | 13.30 | % on polymer |
| Iron oxide yellow |  | 2.42 | % on polymer |
| Dibutyl sebacate | 16.87 | 17.0 | % on polymer |
| Acetone/Isopropanol | 51:49 | — | ratio |
| Acetone/Isopropanol/Water |  | 49:47:5 | ratio |
| Solid content | 6.78 | 13.01 | % |

TABLE 3

| Example 2 | Pre-isolation Layer | Functional Layer |
| --- | --- | --- |
| EUDRAGIT ® S 12.5 |  | 3.60 | mg/cm² |
| EUDRAGIT ® L 12.5 | 0.19 | 2.40 | mg/cm² |
| Talc Pharma |  | 27.45 | % on polymer |
| Iron oxide red |  | 13.30 | % on polymer |
| Iron oxide yellow |  | 2.42 | % on polymer |
| Dibutyl sebacate | 16.87 | 17.0 | % on polymer |
| Acetone/Isopropanol | 51:49 | — | ratio |
| Acetone/Isopropanol/Water |  | 49:47:5 | ratio |
| Solid content | 6.78 | 13.01 | % |

TABLE 4

| Example 3 | Pre-isolation Layer | Functional Layer |  |
| --- | --- | --- | --- |
| EUDRAGIT ® S 12.5 |  | 3.00 | mg/cm² |
| EUDRAGIT ® L 12.5 | 0.19 | 3.00 | mg/cm² |
| Talc Pharma |  | 27.45 | % on polymer |
| Iron oxide red |  | 13.30 | % on polymer |
| Iron oxide yellow |  | 2.42 | % on polymer |
| Dibutyl sebacate | 16.87 | 17.0 | % on polymer |
| Acetone/Isopropanol | 51:49 | — | ratio |
| Acetone/Isopropanol/Water |  | 49:47:5 | ratio |
| Solid content | 6.78 | 13.01 | % |

TABLE 5

| Example 4 | Pre-isolation Layer | Functional Layer |  |
| --- | --- | --- | --- |
| EUDRAGIT ® S 12.5 |  | 2.40 | mg/cm² |
| EUDRAGIT ® L 12.5 | 0.19 | 3.60 | mg/cm² |
| Talc Pharma |  | 27.45 | % on polymer |
| Iron oxide red |  | 13.30 | % on polymer |
| Iron oxide yellow |  | 2.42 | % on polymer |
| Dibutyl sebacate | 16.87 | 17.0 | % on polymer |
| Acetone/Isopropanol | 51:49 | — | ratio |
| Acetone/Isopropanol/Water |  | 49:47:5 | ratio |
| Solid content | 6.78 | 13.01 | % |

Capsule formulations were then prepared by filling four coated mesalamine 100 mg mini-tablets in a HPMC capsule (size 0el or size 0). In order to observe a pH selective profile (i.e., a pH dissolution profile illustrating release at selective pHs), tablets with different formulations and thus different trigger pH values were chosen. Table 6 sets forth the various capsules that were tested and their trigger pH. The dissolution method was as described above.

TABLE 6

| Example Nos. | Ratio (L:S) | Trigger pH | FIG. No. |
| --- | --- | --- | --- |
| Example 1_6 mg/cm² + | 0:10 | pH 7.0 | 1 |
| Example 4_6 mg/cm² | 6:4 | pH 6.4 |  |
| Example 1_6 mg/cm² + | 0:10 | pH 7.0 | 2 |
| Example 3_6 mg/cm² | 5:5 | pH 6.5 |  |
| Example 1_6 mg/cm² + | 0:10 | pH 7.0 | 3 |
| Example 3_5 mg/cm² | 5:5 | pH 6.5 |  |
| Example 1_6 mg/cm² + | 0:10 | pH 7.0 | 4 |
| Example 2_5 mg/cm² | 4:6 | pH 6.6 |  |

Figure 2:
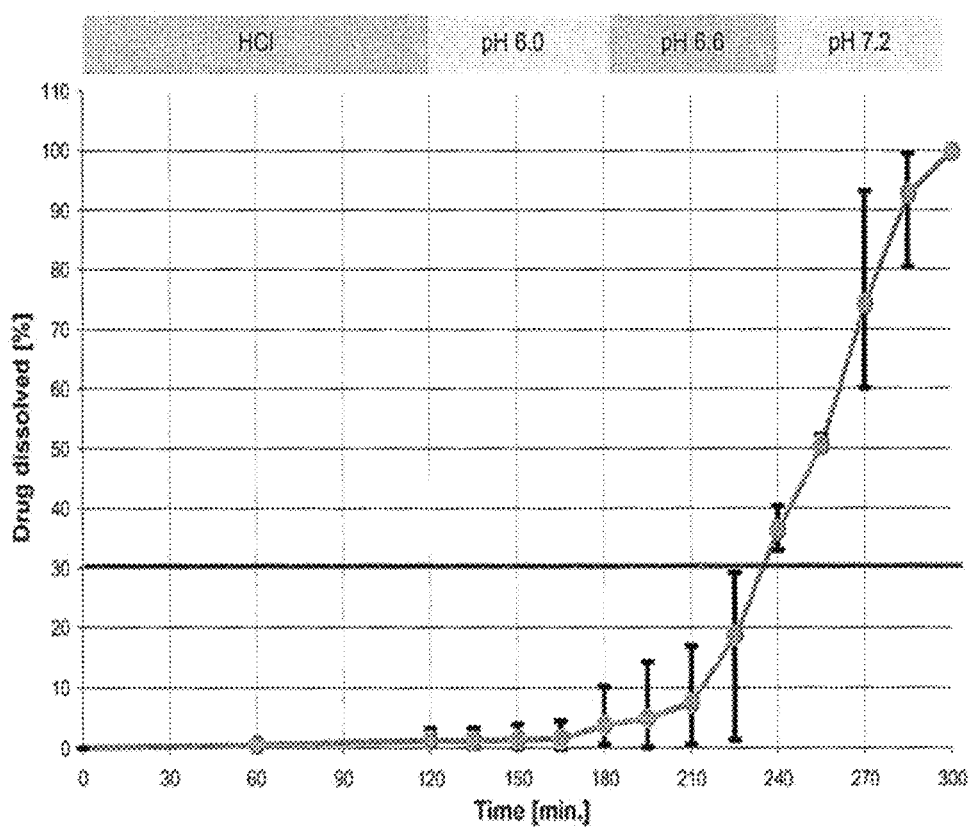
FIG. 2 is a plot depicting the dissolution profile of a mesalamine pharmaceutical composition of another embodiment of the present invention.
Figure 3:
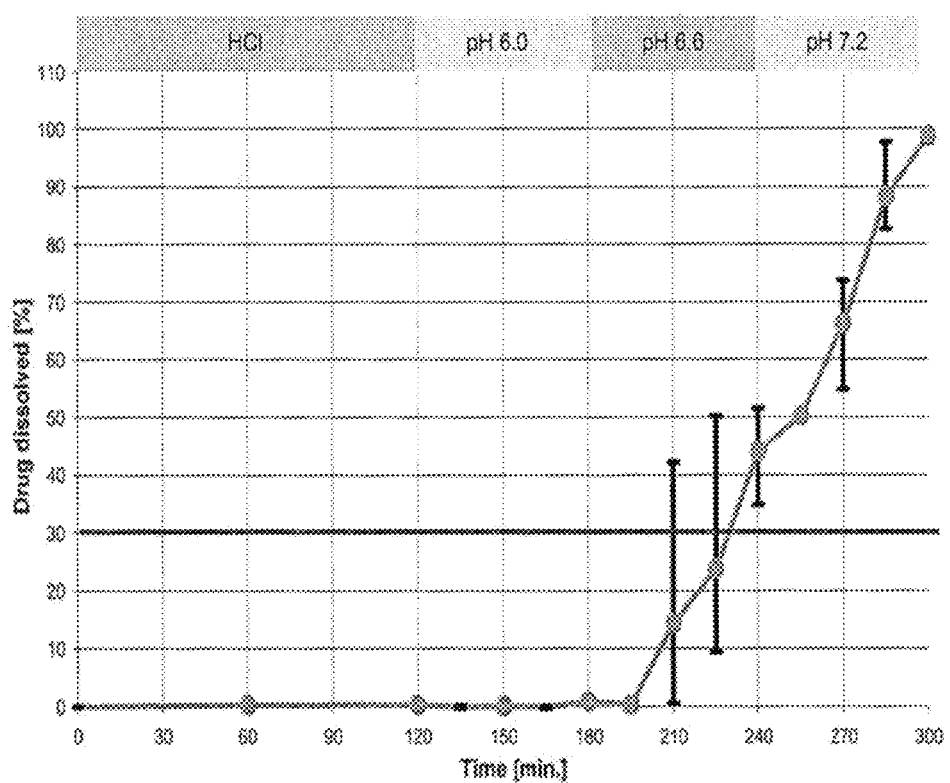
FIG. 3 is a plot depicting the dissolution profile of a mesalamine pharmaceutical composition of yet another embodiment of the present invention.
Figure 4:
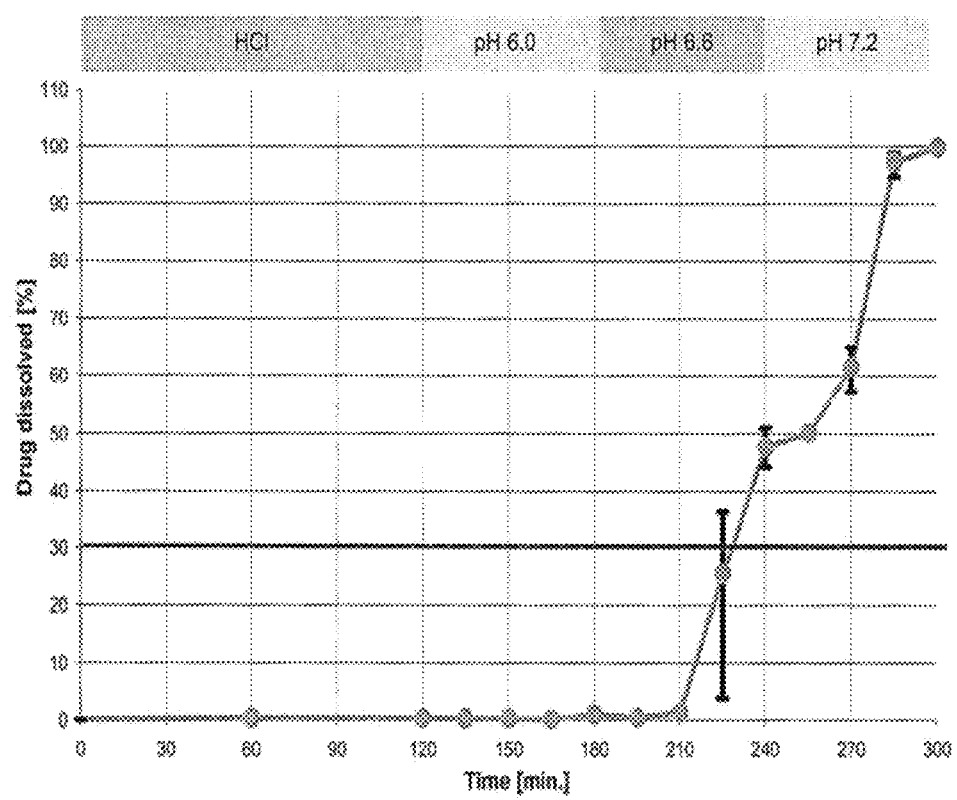
FIG. 4 is a plot depicting the dissolution profile of a mesalamine pharmaceutical composition of yet another embodiment of the present invention.

The dissolution profiles of the formulations set forth in Table 6 are shown in FIGS. 1-4, respectively. As seen in FIGS. 1-4, all dissolution profiles showed enteric properties and resistance in the first buffer stage pH 6.0. The pH selective profile can be clearly seen in FIGS. 1-4. As seen in FIGS. 1-4, in each capsule, the two tablets with formulations having a lower trigger pH (Example 4_6 mg/cm², Example 3_6 mg/cm², Example 3_5 mg/cm², Example 2_5 mg/cm²) showed at least 70% drug release (35% of total drug dissolved) in the phosphate buffer pH 6.6 from those low trigger tablets. Also as seen in FIGS. 1-4, in each capsule, the remaining two tablets with formulations having a higher trigger pH (Example 1_6 mg/cm²) show release in the phosphate buffer pH 7.2.

The following Points are non-limiting second embodiments of the present invention:

Point 1. A mesalamine pharmaceutical composition for delivery of mesalamine to the colon with reduced delivery variability, the composition comprising (i) at least one first dosage element comprising a first mesalamine dose and a first enteric coating and (ii) at least one second dosage element comprising a second mesalamine dose and a second enteric coating, wherein the first enteric coating is soluble at a pH of about 5.9 to less than about 6.4 in an aqueous phosphate buffer and the second enteric coating is soluble in an aqueous phosphate buffer at a pH of 0.2 to 1.3 units higher than the first enteric coating, wherein the solubility of the first and second enteric coating in aqueous phosphate buffer is determined after an initial exposure of the composition in 0.1 N hydrochloric acid for 2 hours at a paddle speed of 100 followed by 1 hour in a 5.5 pH phosphate buffer at a paddle speed of 100 rpm.

Point 2. The mesalamine pharmaceutical composition of Point 1, wherein the at least one first dosage element containing about 30% to about 70% by weight of the total mesalamine in the composition and the at least one second dosage element contains about 30% to about 70% by weight of the total mesalamine in the composition.

Point 3. The mesalamine pharmaceutical composition of Point 2, wherein the at least one first dosage element containing about 50% by weight of the total mesalamine in the composition and the at least one second dosage element contains about 50% by weight of the total mesalamine in the composition.

Point 4. The mesalamine pharmaceutical composition of Point 1, wherein the at least one first dosage element releases mesalamine in an amount of at least about 30% to about 60% by weight of the total mesalamine in the composition over 60 minutes at a pH of about 6.0 in an aqueous phosphate buffer using a paddle apparatus 2 with a paddle speed of 100 rpm, and the at least one second dosage element releases mesalamine in an amount of at least about 40% to about 70% by weight of the total mesalamine in the composition over 60 minutes at a pH of about 6.6 in an aqueous phosphate buffer using a paddle apparatus 2 with a paddle speed of 100 rpm.

Point 5. The mesalamine pharmaceutical composition of Point 4, wherein the first dosage element releases about 40% to about 50% by weight of the composition over 60 minutes at a pH of about 6.0.

Point 6. The mesalamine pharmaceutical composition of Point 2, wherein the pH at which the second enteric coating is soluble is 0.4 to 0.8 higher than the pH at which the first enteric coat is soluble.

Point 7. The mesalamine pharmaceutical composition of Point 3, wherein the pH at which the second enteric coating is soluble is 0.5 to 0.6 higher than the pH at which the first enteric coat is soluble.

Point 8. The mesalamine pharmaceutical composition of Point 4, wherein the composition comprises a capsule containing two first dosage elements and two second dosage elements.

Point 9. The mesalamine pharmaceutical composition of Point 8, wherein the enteric coating of the first dosage element is different from the enteric coating of the second dosage element.

Point 10. The mesalamine pharmaceutical composition of Point 9, wherein the first enteric coating is a mixture of poly(methacrylic acid, co-ethyl acrylate) 1:1 and poly(methacrylic acid, co-methyl methacrylate) 1:1 and the second enteric coating is selected from the group consisting of poly(methacrylic acid, methyl methacrylate) 1:2 and poly(methacrylic acid, methyl methacrylate) 1:1.

Point 11. The mesalamine pharmaceutical composition of Point 10, wherein the mixing weight ratio of the first enteric coating is 9:1 to 1:9.

Point 12. The mesalamine pharmaceutical composition of Point 11, wherein the mixing weight ratio of the first enteric coating is 6:4 to 4:6.

Point 13. The mesalamine pharmaceutical composition of Point 12, wherein the mixing weight ratio of the first enteric coating is about 5:5.

Point 14. A mesalamine pharmaceutical composition for delivery of mesalamine to the colon with reduced delivery variability, the composition comprising (i) at least one first dosage element comprising a first mesalamine dose and a first enteric coating and (ii) at least one second dosage element comprising a second mesalamine dose and a second enteric coating, wherein the first enteric coating is soluble at a pH of about 6.0 to less than about 6.4 in an aqueous phosphate buffer and the second enteric coating is soluble in an aqueous phosphate buffer at a pH of 0.9 to 1.1 units higher than the first enteric coating, wherein the solubility of the first and second enteric coating in aqueous phosphate buffer is determined after an initial exposure of the composition in 0.1 N hydrochloric acid for 2 hours at a paddle speed of 100 followed by 1 hour in a 5.5 pH phosphate buffer at a paddle speed of 100 rpm.

Point 15. The mesalamine pharmaceutical composition of Point 14, wherein the at least one first dosage element containing about 30% to about 70% by weight of the total mesalamine in the composition and the at least one second dosage element contains about 30% to about 70% by weight of the total mesalamine in the composition.

Point 16. The mesalamine pharmaceutical composition of Point 15, wherein the at least one first dosage element containing about 50% by weight of the total mesalamine in the composition and the at least one second dosage element contains about 50% by weight of the total mesalamine in the composition.

Point 17. The mesalamine pharmaceutical composition of Point 14, wherein the at least one first dosage element releases mesalamine in an amount of at least about 30% to about 60% by weight of the total mesalamine in the composition over 60 minutes at a pH of about 6.0 in an aqueous phosphate buffer using a paddle apparatus 2 with a paddle speed of 100 rpm, and the at least one second dosage element releases mesalamine in an amount of at least about 40% to about 70% by weight of the total mesalamine in the composition over 60 minutes at a pH of about 7.0 in an aqueous phosphate buffer using a paddle apparatus 2 with a paddle speed of 100 rpm.

Point 18. The mesalamine pharmaceutical composition of Point 17, wherein the first dosage element releases about 40% to about 50% by weight of the composition over 60 minutes at a pH of about 6.0.

Point 19. The mesalamine pharmaceutical composition of Point 17, wherein the composition comprises a capsule containing two first dosage elements and two second dosage elements.

Point 20. The mesalamine pharmaceutical composition of Point 19, wherein the enteric coating of the first dosage element is different from the enteric coating of the second dosage element.

Point 21. The mesalamine pharmaceutical composition of Point 20, wherein the first enteric coating is a mixture of poly(methacrylic acid, methyl methacrylate) 2:1 and poly(methacrylic acid, methyl methacrylate) 1:1 and the second enteric coating is selected from the group consisting of poly(methacrylic acid, methyl methacrylate) 1:2 and poly(methacrylic acid, methyl methacrylate) 1:1.

Point 22. The mesalamine pharmaceutical composition of Point 21, wherein the mixing weight ratio of the first enteric coating is 9:1 to 1:9.

Point 23. The mesalamine pharmaceutical composition of Point 22, wherein the mixing weight ratio of the first enteric coating is 6:4 to 4:6.

Point 24. The mesalamine pharmaceutical composition of Point 25, wherein the mixing weight ratio of the first enteric coating is about 5:5.

While the invention has been described above with reference to specific embodiments thereof, it is apparent that many changes, modifications, and variations can be made without departing from the inventive concept disclosed herein. Accordingly, it is intended to embrace all such changes, modifications, and variations that fall within the spirit and broad scope of the appended claims. All patent applications, patents, and other publications cited herein are incorporated by reference in their entirety.

What is claimed is:

1. A mesalamine pharmaceutical composition for delivery of mesalamine to the colon with reduced delivery variability, the composition consisting essentially of a capsule containing (i) at least one first dosage element comprising a first mesalamine dose and a first enteric coating and (ii) at least one second dosage element comprising a second mesalamine dose and a second enteric coating, wherein the first enteric coating is soluble at a pH of about 6.4 to about 6.8 in an aqueous phosphate buffer and the second enteric coating is soluble in an aqueous phosphate buffer at a pH of 0.2 to 1 units higher than the first enteric coating, wherein the solubility of the first and second enteric coating in aqueous phosphate buffer is determined after an initial exposure of the composition in 0.1 N hydrochloric acid for 2 hours at a paddle speed of 100 followed by 1 hour in a 6.0 pH phosphate buffer at a paddle speed of 100 rpm and the first enteric coating of the first dosage element and second enteric coating of the second dosage element are soluble at the pH in aqueous phosphate buffer such that after 60 minutes at least 70% of the mesalamine has been released from said dosage element using a paddle apparatus 2 with a paddle speed of 100 rpm and wherein the combined number of first dosage element contains about 50% by weight of the total mesalamine in the composition and the at least one second dosage element contains about 50% by weight of the total mesalamine in the composition.

2. The mesalamine pharmaceutical composition of claim 1, wherein the at least one first dosage element releases mesalamine in an amount of at least about 30% to about 50% by weight of the total mesalamine in the composition over 60 minutes at a pH of about 6.6 in an aqueous phosphate buffer using a paddle apparatus 2 with a paddle speed of 100 rpm, and the at least one second dosage element releases mesalamine in an amount of at least about 40% to about 50% by weight of the total mesalamine in the composition over 60 minutes at a pH of about 7.2 in an aqueous phosphate buffer using a paddle apparatus 2 with a paddle speed of 100 rpm.

3. The mesalamine pharmaceutical composition of claim 2, wherein the first dosage element releases about 40% to about 50% by weight of the composition over 60 minutes at a pH of about 6.6.

4. The mesalamine pharmaceutical composition of claim 1, wherein the pH at which the second enteric coating is soluble is 0.4 to 0.8 higher than the pH at which the first enteric coat is soluble.

5. The mesalamine pharmaceutical composition of claim 1, wherein the pH at which the second enteric coating is soluble is 0.5 to 0.6 higher than the pH at which the first enteric coat is soluble.

6. The mesalamine pharmaceutical composition of claim 2, wherein the capsule contains two first dosage elements and two second dosage elements.

7. The mesalamine pharmaceutical composition of claim 6, wherein the enteric coating of the first dosage element is different from the enteric coating of the second dosage element.

8. The mesalamine pharmaceutical composition of claim 7, wherein the first enteric coating is a mixture of poly(methacrylic acid, methyl methacrylate) 1:2 and poly(methacrylic acid, methyl methacrylate) 1:1 and
the second enteric coating is selected from the group consisting of poly(methacrylic acid, methyl methacrylate) 1:2 and poly(methacrylic acid, methyl methacrylate) 1:1.

9. The mesalamine pharmaceutical composition of claim 8, wherein the mixing weight ratio of the first enteric coating is 9:1 to 1:9.

10. The mesalamine pharmaceutical composition of claim 9, wherein the mixing weight ratio of the first enteric coating is 6:4 to 4:6.

11. The mesalamine pharmaceutical composition of claim 10, wherein the mixing weight ratio of the first enteric coating is about 5:5.

* * * * *